USOO5688641A

United States Patent [19]
Sager et al.

[11] Patent Number: 5,688,641
[45] Date of Patent: Nov. 18, 1997

[54] CANCER DIAGNOSIS USING NUCLEIC ACID HYBRIDIZATION

[75] Inventors: Ruth Sager, Brookline, Mass.; Zhiqiang Zou, Gaithersburg, Md.; Sam Whan Lee, Newton, Mass.; Catherine Laure Tomasetto, Strasbourg, France

[73] Assignee: Dana-Farber Cancer Institute, Inc., Boston, Mass.

[21] Appl. No.: 322,742

[22] Filed: Oct. 13, 1994

Related U.S. Application Data

[63] Continuation of Ser. No. 938,823, Sep. 1, 1992, abandoned, which is a continuation-in-part of Ser. No. 844,296, Feb. 28, 1992, abandoned, which is a continuation-in-part of Ser. No. 662,216, Feb. 28, 1991, abandoned.

[51] Int. Cl.$^6$ .................................. C12Q 1/68
[52] U.S. Cl. .................. 435/6; 435/40.5; 436/503; 436/811
[58] Field of Search .................. 436/501, 503, 436/811; 435/6, 40.5; 530/350; 536/23.5

[56] References Cited

U.S. PATENT DOCUMENTS

| | | | |
|---|---|---|---|
| 4,888,278 | 12/1989 | Singer et al. | 435/6 |
| 5,049,662 | 9/1991 | Steeg | 536/27 |
| 5,115,096 | 5/1992 | Shoyab et al. | 530/322 |

OTHER PUBLICATIONS

Ciardiello et al., PNAS 88(17):7792–6, Sep. 1, 1991.
Wildrick et al. Anticancer Res. 12(5):1271–4, Sep./Oct. 1992.
R. Sager et al., Cold Spring Harbor Symposia on Quantitative Biology, vol. LIX:537–546, 1994.
Tomasetto et al., "Specificity of Gap Junction Communication Among Human Mammary Cells and Connexin Transfectants in Culture", J. Cell Biol. 122:157–167 (1993).
Swaroop et al., "A Simple and Efficient cDNA Library Subtraction Procedure: Isolation of Human Retina–Specific cDNA Clones", Nucl. Acids Res. 19:1954 (1991).
Schweinfest et al., "Subtraction Hybridization cDNA Libraries from Colon Carcinoma and Hepatic Cancer", Genet. Annal. Techn. Appl. 7:64–70.
Cattaneo et al., Altered Ratios of Measles Virus Transcripts in Diseased Human Brains, Biology 160:523–526, 1987.
Band et al., Gene, Chromosomes & Cancer 1:48–58, 1989.
Band and Sager, Proc. Natl. Acad. Sci. USA 86:1249–1253, 1989.
Band et al., Cancer Research 50:7351–7357, 1990.
Baylin et al., Blood 70:412–417, 1987.
Calabretta et al., The Journal of Biological Chemistry 261:12628–12632, 1986.
Carr et al., Carcinogenesis 5:1583–1590, 1984.
Cowan et al., Proc. Natl. Acad. Sci. USA 83:9328–9322, 1986.
El–Deiry et al., Proc. Natl. Acad. Sci. USA 88:3470–3474, 1991.
Friedmann, Molecular Medicine Therapy for Genetic Disease, ed. by Theodore Friedmann, pp. 107–121.

Gibbs et al., Nucleic Acids Research 18:4401–4407, 1990.
Harrison et al., Proc. Natl. Acad. Sci. USA 80:6606–6610, 1983.
Jones and Buckley, Advances in Cancer Research 54:1–23, 1990.
Kligman and Hilt, TIBS 13:437–443, 1988.
Lee et al., Pro. Natl. Acad. Sci. USA 88:2825–2829, 1991.
Lee et al., Molecular and Cellular Biology 10:1982–1988, 1990.
Lersch and Fuchs, Molecular and Cellular Biology 8:486–493, 1988.
Moscow et al., Cancer Research 49:1422–1428, 1989.
Sager, Science 246:1406–1412, 1989.
Trask et al., Proc. Natl. Acad. Sci. USA 87:2319–2323, 1990.
Yaswen et al., Proc. Natl. Acad. Sci. USA 87:7360–7364, 1990.
Zhang and Nicholson, J. Cell. Biol. 109–3391–3401, 1989.
Wiedow et al., J. Biological Chemistry 265:14791–14795, 1990.
Tsunemi et al., Biochemical and Biophysical Research Communications 185:967–973, 1992.
Saheki et al., Biochemical and Biophysical Research Communications 185:240–245, 1992.
Lee et al., Proc. Natl. Acad. Sci. 89:2504–2508, 1992.
Remold–O'Donnell et al., Proc. Natl. Acad. Sci. 89:5635–5639, 1992.

*Primary Examiner*—Stephen Walsh
*Assistant Examiner*—Lorraine M. Spector
*Attorney, Agent, or Firm*—Fish & Richardson P.C.

[57] ABSTRACT

A method of determining whether a test cell from a given human tissue type is (a) normal, or (b) cancerous or precancerous, by contacting the mRNA of the test cell with a nucleic acid probe which contains a nucleotide sequence at least 15 nucleotides in length which is complementary to a portion of the coding sequence of a candidate tumor suppressor gene, which gene is one that is expressed at a given control level in normal cells of that tissue type; and determining the approximate amount of hybridization of the probe to the mRNA of the test cell, an amount of hybridization one-third or less that seen with the mRNA of a normal cell of that tissue type being an indication that the test cell is cancerous or precancerous. Alternatively, an antibody specific for the candidate tumor suppressor gene product can be substituted for the nucleic acid probe as a means for determining the level of expression of the gene in the test cell. The invention also includes methods of treating a cancerous cell by increasing the level of expression of a candidate tumor suppression gene in the cell; novel candidate tumor suppressor genes; and their use in diagnosis, prognosis, and therapy.

10 Claims, 2 Drawing Sheets

```
                                    GATTAATCCTATGACAAACTAAGTT  -175

GGTTCTGTCTCTTCACCTGTGTTTGGTGAGGTTGTGTGTAAGAGTTGGTGTGTTTGCTCAGGAAGAGATTTAAGCATGCTTGCTTACCCAGACT  -88

CAGAGAAGTCTCCCTGTCCTAGCTAGTGATTCCTGTGTGTGCATTCGTCTTTTCCAGACAACCGCCCAGAGTAGAAG  -1

1  ATG GAT TGG GGC ACG CTG CAG ATC ACG CTG GGG GGT GTG AAC AAA CAC TCC ACC AGC ATT GGA AAG    66
     M   D   W   G   T   L   Q   I   T   L   G   G   V   N   K   H   S   T   S   I   G   K

23  ATC TGG CTC ACC GTC CTC TTC ATT TTT CGC ATG ATC CTG CAG CCA GTG GCT GCA AAG GAG GTG TGG   132
     I   W   L   T   V   L   F   I   F   R   M   I   L   Q   P   V   A   A   K   E   V   W

45  GGA GAT GAG CAG TAT GCC GAC TTT GTC TGC AAC ACC CTG CAG GGC TGC AAG AAC GTG TAC GAT        198
     G   D   E   Q   Y   A   D   F   V   C   N   T   L   Q   G   C   K   N   V   Y   D

67  CAC TAC TTC CCC ATC TCC CAC ATC CGG CTA TGG CAG CTG ATC TTC GTG TCC AGC CCA GCG            264
     H   Y   F   P   I   S   H   I   R   L   W   Q   L   I   F   V   S   S   P   A

89  CTC CTA GTG GCC ATG CAC GTG GCC TAC CGG AGA CAT GAG AAG AAG TTC ATC AAG GGG GAG            330
     L   L   V   A   M   H   V   A   Y   R   R   H   E   K   K   F   I   K   G   E

111  ATA AAG AGT GAA TTT AAG GAC ATC GAG GAG ATC AAA ACC CAG AAG GTC CGC ATC GAA GGC TCC CTG    396
     I   K   S   E   F   K   D   I   E   E   I   K   T   Q   K   V   R   I   E   G   S   L

133  TGG TGG ACC TAC ACA TAC TCC AGC AGC ATC TTC CGG GTC ATC TTC GAA GCC TTC ATG TAC GTC TTC    462
     W   W   T   Y   T   Y   S   S   S   I   F   R   V   I   F   E   A   F   M   Y   V   F

155  TAT GTC GAC TAC ATG TAC TCC ATG CAG CGG CTG GTG AAG TGC TGG CCT TGT CCC AAC                528
     Y   V   D   Y   M   Y   S   M   Q   R   L   V   K   C   W   P   C   P   N

177  ACT GTG GAC TTT GTG TCC CGG GAG ACG GAG AAG ACT GTC TTC ATT GCA GTG                        594
     T   V   D   F   V   S   R   E   T   E   K   T   V   F   M   I   A   V

199  TCT GGA ATT TGC ATC CTG CTG AAT GTC ACT GAA TTG TGT TAT TTG CTA ATT AGA TAT TGT TCT GGG    660
     S   G   I   C   I   L   L   N   V   T   E   L   C   Y   L   L   I   R   Y   C   S   G

221  AAG TCA AAA AAG CCA GTT TAA                                                                681
     K   S   K   K   P   V   -

FIG. 1A
```

```
CGCATTGCCCAGTTGTTAGAGATTAAGAAATAGACAGCATGAGAGGGATGAGGCAACCCGTGCTCAGTCGTCAAGGCTCAGTCGCCAGC  768
ATTTCCCAACACAAAGATTCTGACCTTAAATGCAACCATTGAACCCCTGTAGGCCTCAGGTGAAACTCCAGATGCCACAATGAGC     855
TCTGCTCCCCTAAAGCCTCAAAACAAAGGCCTAATTCTATGCCGTCTTAATTTCTTTCACTTAAGTTCCACTGAGACCCCA         942
GGCTGTTAGGGGTTATTGGTGTAAGGTACTTCATATTTTAAACAGAGGATATCGGCATTTGTTCTTCTTCTGAGGACAAGAGAAA    1029
AAGCCCAGGTTCCACAGAGGACACAGAAGTTTGGGTGTCCTCCTGGGGTTCTTTTTGCCAACTTCCCCACGTTAAAGTGAAC       1116
ATTGGTTCTTTCATTGTATGATAGGTTATTTTGATGTAAAGATGTTCTGGATACCATTATATGTCTTAAACTCTGTTACACTTTTGAA  1203
GTGAAACTTGTAGTATGATATGTCATTCATTGGTATTCGCTACTATGATTTAATTTGAAATATGGTCTTTTGGTTATGAATACTTGCAGCACAGCTGA  1290
TGTAATATGTAAATGGTATGTGTATTCATTCATTGGTATTCGCTACTATGATTTAATTTGAAATATGGTCTTTTGGTTATGAATACTTGCAGCACAGCTGA  1377
AGGGAGCTGTCTGTTGATAGCAAATGGCCTCATGTCAAATATTAGAGTCACCTAACAACATTGTAGCCTGAGTCGAGTCAGACAGACTAGAAGTTCCTAGT  1464
TGGCTTATGATGACAAATGGCCTCATGTCAAATATTAGAGTCACCTAACAACATTGTAGCCTGAGTCGAGTCAGACAGACTAGAAGTACCAACTACTAC  1551
CTGTAATGACAGGCCCTGTCCAACACATCTCCCTTTCCATGCTGTGGTAGCCAGCATCGGAAAGAACGCTGATTTAAAGAGGTGAGC   1638
TTGGAATTTATTGACACAGTACCATTTAATGGGGAGACAAAATGGGGGCCAGGGAGACAAAGTTTCTGTCGTTAAAACGAG        1725
TTTGGAAAGACTGGACTCTAAATTCTGTTGATTAAGATGAGCTTTGTCTACCTTCACCCCCCTTCAGCCTC                   1812
CAATTTTTAAGCTGAATGAAATATAACTAATAACATGTGAAAGAATAGAAGCTAAGGTTTAGATAATACTTCAGTGAGGTAGAAG    1899
ATTGAACCTGAATATTGCCATTATGCTTGACATGGTTTCCAAAAAATGTACTCCACATACTTCAGTGAGGGTAAGTATTTTCCTGT   1986
TGTCAAGAATAGCATTGTAAAAGCATTTGTAATAATAAGAATAGCTTTAATGATATGCTTGTAACTAACTAAAATAATTTGTAATGTA  2073
TCAAATACATTAAAACATTAAAATATAAATCTCTATAAT                                                    2112
```

FIG. 1B

CANCER DIAGNOSIS USING NUCLEIC ACID HYBRIDIZATION

This application is a continuation of U.S. Ser. No. 07/938,823, filed Sep. 1, 1992, and now abandoned, which is a continuation-in-part of U.S. Ser. No. 07/844,296, filed Feb. 28, 1992, and now abandoned, which in turn is a continuation-in-part of U.S. Ser. No. 07/662,216, filed Feb. 28, 1991, and now abandoned.

The invention was made with support from the National Institute of Health, specifically Grant No. CA39814. The U.S. government has rights in the invention.

BACKGROUND OF THE INVENTION

This invention relates to diagnosis, prognosis, and treatment of cancers, particularly, solid tumors.

Sager, 246 *Science* 1406, 1989, discusses tumor suppressor genes. The loss of tumor suppressor genes, or their inactivation, is oncogenic. That is, the loss of DNA encoding a tumor suppressor gene product, or the lowering of expression of a tumor suppressor gene, gives rise to a cancerous condition. Sager generally describes the identification of candidate tumor suppressor genes. In particular, Sager describes the process of subtractive hybridization as a general method for recovering genes that are expressed in normal cells but not in closely related tumor cells. Sager further describes the isolation of three clones by subtractive hybridization of normal and cancerous mammary cells. The genes corresponding to these clones are expressed by normal mammary epithelial cells, but not by any primary mammary tumors or mammary tumor cell lines tested. Three such genes encode keratin 5, fibronectin, and NB-1, which are said to be valuable markers to distinguish normal and primary tumor cells in culture. Tumor suppressor genes are proposed to play a key role in cancer protection, and it is suggested that tumor suppressor genes provide a vast untapped resource for anti-cancer therapy.

Decreased DNA methylation is a consistent feature of tumorigenesis (Jones et al., *Adv. Cancer Res.* 54:1–23, 1990) but local sites of hypermethylation have also been found in tumor cells (Jones et al., *Adv. Cancer Res.* 54:1–23, 1990; Baylin et al., *Blood* 70:412–417, 1987). Elevated expression of the DNA methyltransferase gene has recently been described in progressive stages of colon cancer (El-Deiry et al., *Proc. Natl. Acad. Sci. USA* 88:3470–3474, 1991), suggesting a general mechanism for hypermethylation, but not explaining the specificity seen on particular genes.

SUMMARY OF THE INVENTION

This invention features novel methods for identifying and/or classifying cancerous cells present in a human, particularly in solid tumors (carcinomas and sarcomas) such as breast, colorectal, gynecological, lung, prostate, bladder, renal, liver, urethral, penal, endocrinal (e.g., multiple endocrine neoplasia), melanoma, basal cell, central nervous system, lymphoma, stomach, esophageal, and squamous cell cancers, as well as solid tumors of childhood (e.g., retinoblastoma). The methods also apply to other cancers, such as leukemias. The method utilizes genes that are preferentially expressed in normal cells compared with related tumor cells, and thereby identifies or classifies tumor cells by the loss of expression of particular genes, an event which is believed to occur early in the process of tumor. The invention also features methods for identifying drugs useful for treatment of such cancer cells, and for treatment of the cancerous condition. Unlike prior methods, the invention provides a means for identifying cancer cells at an early stage of development, so that premalignant cells can be identified prior to their spreading throughout the human body. This allows early detection of potentially cancerous conditions, and treatment of those cancerous conditions prior to spread of the cancerous cells throughout the body, or prior to development of an irreversible cancerous condition.

Tumor suppressor genes have been divided into two general types, termed class I and class II. Class I tumor suppressor genes are said to be those in which a genetic alteration (e.g., the deletion, addition or substitution of one or more nucleotides) in the coding sequence of the gene has been found to contribute to tumor cell development. In contrast, class II tumor suppressor genes are identified as those which have a lower level of expression in a cancer or precancer cell compared to a normal cell, which decreased level of expression is due to alteration in the regulation of expression of that gene, rather than to the loss of genetic information in the coding sequence of that gene. A diagnostic test based upon levels of expression of either a class I or a class II gene, or of another marker gene that is identified as a candidate tumor suppressor gene by one of the differential screening methods described below, but which does not turn out to have tumor suppressor activity, is useful for detecting the presence of cancerous or pre-cancerous cells in a tissue sample from a patient. In addition, a patient with a cancer characterized by a lower-than-normal level of expression of one or more tumor suppressor genes can be treated [e.g., with a drug or radiation, or by introducing (as by transfection) one or more of the tumor suppressor genes into the cancerous cells] to induce a higher level of expression of such gene(s) in the cancerous cells, thus halting or reversing the growth of the cancer.

In a first aspect, the invention features a method for identifying cancer cells in a human by providing nucleic acid from a candidate tumor suppressor gene which specifically hybridizes to RNA expressed from such a gene in a cancer cell at a level less than one third the level of hybridization with the equivalent RNA expressed from that gene in a normal cell. Alternatively, the method involves providing an antibody to the gene product of such a candidate tumor suppressor gene, which antibody specifically reacts (in the sense of an antibody-antigen reaction to form an immunocomplex) with the polypeptide expressed from the candidate tumor suppressor gene in a cancer cell, at a level less than one-third the level of reaction (i.e., binding) with the equivalent gene product expressed from that gene in a normal cell. The method further features obtaining from the human a tissue sample which potentially includes the cancer cell to be detected, and contacting this sample with either (1) the nucleic acid probe, under conditions which would permit hybridization with the mRNA transcribed from the gene (for example, as in a Northern blot or in situ hybridization of a tissue sample), or (2) the antibody, under conditions appropriate for immune complex formation between the antibody and its antigen (for example, by immunoprecipitation techniques, immunostaining in situ, or Western blot). Finally, the method involves determining the amount of hybridization of the nucleic acid or the amount of binding of the antibody with the tissue sample, compared to the amount of hybridization of that nucleic acid or binding of that antibody with a normal tissue sample which includes only normal cells. An amount of hybridization or immune complex formation with the tissue sample less than one third the amount of hybridization or immunocomplex formation with the normal tissue sample is indicative of the presence of cancerous or pre-cancerous cells in the tissue sample.

Tumor tissue samples frequently contain a mixture of normal and tumor cells. For a positive detection of tumor cells in such samples, the decrease in hybridization or immunocomplex formation should be proportional to the fraction of tumor cells in the sample, consistent with other evidence available to the clinician such as the pathology report. In such cases, the principal utility of the method described above is as supporting evidence validating the diagnosis of cancer, or as a means for classifying or staging the tumor cells as an aid to prognosis and determination of the optimal means of therapy.

In practice, the method of using a nucleic acid probe to determine the presence of cancerous cells in a tissue from a patient includes the steps of providing a nucleic acid probe (i.e., a single-stranded nucleic acid such as DNA, or a double stranded nucleic acid which is made single-stranded prior to doing the hybridization step) comprising a nucleotide sequence at least 8 nucleotides in length (preferably at least 15 nucleotides, and more preferably at least 40 nucleotides, and up to all or nearly all of the coding sequence) which is complementary to a portion of the coding sequence of a candidate tumor suppressor gene;

obtaining from a patient a first tissue sample potentially comprising cancerous cells;

providing a second tissue sample containing cells substantially all of which are non-cancerous;

contacting the nucleic acid probe under high-stringency hybridizing conditions with RNA of each of said first and second tissue samples (e.g., in a northern blot or in situ hybridization assay); and comparing (a) the amount of hybridization of the probe with RNA of the first tissue sample, with (b) the amount of hybridization of the probe with RNA of the second tissue sample, wherein an amount of hybridization with the RNA of the first tissue sample less than one-third the amount of hybridization with the RNA of the second tissue sample indicates the presence of cancerous cells in the first tissue sample. This method is useful where the cancerous or precancerous cells in which the candidate tumor suppressor gene has been shut off predominate in the tissue sample. Where other available evidence (e.g., a pathology report) indicates that the tumor cells constitute a given proportion of the sample that is significantly less than all of the tissue sample, the method of the invention is adapted to account for the presence of normal cells in the sample: i.e., a total amount of hybridization in the entire sample that reflects normal levels of expression by the number of normal cells in the sample, plus hybridization at one-third or less of the normal level times the number of tumor cells in the sample, will provide corroborating evidence that the cells predicted by the pathology report to be tumor cells in fact are tumor cells, and in fact are tumor cells of a type characterized by partial or complete loss of expression of the particular candidate tumor suppressor gene probed. This method of confirming a diagnosis that a given fraction of cells in a tissue sample are cancerous or precancerous involves the steps of contacting the mRNA of the sample with the nucleic acid probe derived from a candidate tumor suppressor gene which is expressed in normal cells of the given tissue at a given control level, and determining the approximate amount of hybridization of the probe to the mRNA, an amount of hybridization approximately equal to the total expected if all of the normal cells in the sample expressed the gene at the control level and all of the cancerous or precancerous cells in the sample expressed the gene at one-third or less of the control level being considered a confirmation of the diagnosis.

A more generally applicable method of the invention would use in situ hybridization with a probe derived from a given candidate tumor suppressor gene to reveal the presence of relatively few cancerous or precancerous cells in a sample containing many normal cells: this method involves contacting the labelled hybridization probe with a sample of a given type of tissue potentially containing cancerous or precancerous cells as well as normal cells, and determining whether the probe labels some cells of the given tissue type to a degree significantly less (e.g., 50% less, or more preferably 80% less) than the degree to which it labels other cells of the same tissue type. Ideally, the probe will fail to hybridize significantly with those cells which are cancerous or precancerous, while clearly labelling the normal cells in the sample.

Also within the invention is a method of determining whether a test cell from a given human tissue type is (a) normal, or (b) cancerous or precancerous, by contacting the mRNA of a test cell with a nucleic acid probe which contains a nucleotide sequence at least 15 nucleotides in length (preferably at least 40 nucleotides, and up to all or nearly all of the coding sequence) which is complementary to a portion of the coding sequence of a candidate tumor suppressor gene, the gene being one which is normally expressed in normal cells of the given tissue type; and determining the approximate amount of hybridization of the probe to the mRNA, an amount of hybridization one-third or less that seen with the mRNA of a normal cell of that tissue type being an indication that the test cell is cancerous or precancerous.

Alternatively, any of the above diagnostic assays may be carried out using antibodies to detect the candidate tumor suppressor gene product, instead of a nucleic acid probe to detect candidate tumor suppressor mRNA. One example of such an assay would include contacting the proteins of the test cell with the antibody specific for the gene product of a candidate tumor suppressor gene, the gene being one which is expressed at a given control level in normal cells of the same tissue type as the test cell, and determining the approximate amount of immunocomplex formation by the antibody and the proteins of the test cell, an amount one-third or less than that seen with the proteins of a normal cell of the same tissue type being an indication that the test cell is cancerous or precancerous. Another such method includes the steps of:

providing an antibody specific for the gene product of a candidate tumor suppressor gene, the gene product being present in cancerous tissue of a given tissue type (e.g., mammary, ovary, bladder, colorectal, or prostate epithelium) at a level less than one third the level of the gene product in noncancerous tissue of the same tissue type;

obtaining from a patient a first sample of tissue of the given tissue type, which sample potentially includes cancerous cells;

providing a second sample of tissue of the same tissue type (which may be from the same patient or from a normal control, e.g. another individual or cultured cells), this second sample containing normal cells and essentially no cancerous cells;

contacting the antibody with protein (which may be partially purified, in lysed but unfractionated cells, or in situ) of the first and second samples under conditions permitting immunocomplex formation between the antibody and any tumor suppressor gene product present in the samples; and comparing (a) the amount of immunocomplex formation in the first sample, with (b) the amount of immunocomplex formation in the second sample, wherein an amount of immunocomplex formation in the first sample less than one third (preferably less than one fourth, and more preferably less than one tenth) the amount of immunocomplex formation in the second sample indicates the presence of cancerous cells in the first sample of tissue. Like the hybridization assay described above, this antibody-based assay can be adapted to account for a given proportion of normal cells in the sample, or can be put into practice as an in situ labelling assay that is informative even where the tumor cells do not make up the majority of the tissue sample tested. In the latter case, a labelled antibody to the candidate tumor suppressor gene product is contacted with a tissue sample potentially containing cancerous or precancerous cells as well as normal cells of the same tissue type, and the degree of labelling of individual cells in the sample is observed. Those cells which are heavily labelled are presumably normal by this test, while those which bind relatively little label [e.g., one-third or less, and preferably one-fourth or less (more preferably 1% or less) of what the normal cells bind], are presumably cancerous or precancerous.

In still another variation on the diagnostic assay of the invention, the level of a candidate tumor suppressor gene product in a biological fluid (e.g., blood or urine) of a person may be determined as a way of monitoring the level of expression of the gene in cells of that person. Such a method would include the steps of obtaining a sample of a biological fluid from the person, contacting the sample (or proteins from the sample) with an antibody specific for a candidate tumor suppressor gene product, and determining the amount of immune complex formation by the antibody, with the amount of immune complex formation being indicative of the level of the gene product in the sample. This determination is particularly instructive when compared to the amount of immune complex formation by the same antibody in a control sample taken from a normal individual or cancer patient, or in one or more samples previously or subsequently obtained from the same person.

In preferred embodiments, any of the methods of the invention can be incorporated into a series of such tests, using hybridization or antibody probes that detect the expression of a number of candidate tumor suppressor genes: e.g., use of a first probe designed to detect expression of a first gene in the sample can be followed by use of a second probe designed to detect expression of a second gene in the sample, or in a different sample from the same source. Because cells from different tumors may shut down expression of different tumor suppressor genes at different times, or not at all, a battery of such tests may be necessary to definitively characterize a given cell sample.

The diagnostic assays described above can be adapted to be used as prognostic assays, as well. Such an application takes advantage of the sensitivity of the assays of the invention to events which take place at characteristic stages in the progression of a tumor. For example, a given candidate tumor suppressor gene may be shut down at a very early stage, perhaps before the cell is irreversibly committed to developing into a malignancy, while another gene is characteristically shut down only at a much later stage. Such a method could involve the steps of contacting the mRNA of a test cell with a nucleic acid probe derived from a given candidate tumor suppressor gene which is expressed at different characteristic levels in cancerous or precancerous cells at different stages of tumor progression, and determining the approximate amount of hybridization of the probe to the mRNA of the cell, such amount being an indication of the level of expression of the gene in the cell, and thus an indication of the stage of tumor progression of the cell; alternatively, the assay can be carried out with an antibody specific for the gene product of the given candidate tumor suppressor gene, contacted with the proteins of the test cell. A battery of such tests will disclose not only the existence and location of a tumor, but also will allow the clinician to select the mode of treatment most appropriate for the tumor, and to predict the likelihood of success of that treatment.

The methods of the invention can also be used to follow the clinical course of a tumor. For example, the assay of the invention can be applied to a tissue sample from a patient; following treatment of the patient for the cancer, another tissue sample is taken and the test repeated. Successful treatment will result in either removal of all cells which have the decreased expression characteristic of the cancerous or precancerous cells, or a substantial increase in expression of the gene in those cells, perhaps approaching or even surpassing normal levels.

By a candidate tumor suppressor gene is meant those genes which are found to be expressed to a significantly higher degree in normal cells than in cancerous or precancerous cells, as generally discussed above. Such a candidate tumor suppressor gene is generally identified by northern analysis or its equivalent (for example, by in situ hybridization) as a gene whose expression is lower in a cancer cell compared to a normal cell. If the gene bears a disabling mutation in its coding sequence, then it is termed a "candidate class I tumor suppressor gene". If the coding sequence of the gene is intact, inasmuch as the DNA forming the exons of that gene is not significantly altered, a southern analysis of such a gene in a cancer cell does not reveal any significant difference in the tumor suppressor coding sequence in a cancer cell compared to a normal cell. In such genes, termed "candidate class II tumor suppressor genes", it is the regulatory mechanism of the gene that is altered in a cancerous cell compared to a normal cell.

Once the candidate class I or class II tumor suppressor gene is demonstrated to play a role in suppressing formation of tumors in vivo or transformation of cells in vitro, it may be referred to as a bona fide "class I tumor suppressor gene" or "class II tumor suppressor gene", rather than as a "candidate". Such class II genes are useful in certain of the treatment methods of the invention, because they retain a viable coding sequence which can potentially be switched on by the appropriate treatment, and such switching on will result in increased tumor suppressing activity within the treated cell. Both class I and class II genes can be introduced into cancer cells or pre-cancerous cells in order to increase their level of expression in such cells, and thus slow or prevent neoplastic growth.

By "hybridizing conditions" is meant conditions under which the nucleic acid used as a probe in the method is able to specifically hybridize with RNA expressed from a candidate tumor suppressor gene without significantly hybridizing to any other RNA expressed from either normal or cancerous human cells (e.g., conditions of high stringency, as described, for example, in Sambrook et al., Molecular Cloning, a laboratory manual, 2nd Ed., Cold Spring Harbor Laboratories, Cold Spring Harbor, N.Y., 1989). In this way, hybridization of the RNA specifically indicates the presence or absence of a candidate tumor suppressor gene transcript (usually mRNA). Similarly, reaction of the antibody with the candidate tumor suppressor gene product (protein) is performed under normal antibody-antigen reaction conditions which allow specific recognition of the candidate tumor suppressor gene product by antibody, with little or no cross-reaction of the antibody with other proteins normally present in the cancerous or normal cells. In this way, measurement of the amount of antigen-antibody immune complex formed in the sample is indicative of the amount of candidate tumor suppressor gene product present in that sample.

In preferred embodiments, the candidate tumor suppressor gene is a gene encoding keratin 5, NB-1 gene product, fibronectin, connexin 26, connexin 43, glutathione-S-transferase pi, CaN19 protein (formerly called clone 19 gene product), small proline-rich (spr-1) protein, amphiregulin, thymosin beta-4, gamma actin, calpactin light chain (p11), HBp17, myosin regulatory light chain, V-Fos transformation effector protein, or one of the following mitochondrial genome-encoded proteins: NADP-dehydrogenase (formerly referred to as URF4), Co III, and ATPase6. The candidate tumor suppressor gene may alternatively be one of the newly-identified genes herein referred to as U1–U10, partial sequences of which are given as SEQ ID NOs: 3–12, respectively; in addition, two longer but still incomplete portions of U1 (separated by a gap in the cDNA) have now been sequenced and are shown in SEQ ID NOs: 16 and 17, respectively, with the former sequence being 5' to the latter in the U1 cDNA. Similarly, two longer but still incomplete portions of U2 (also separated by a gap) are provided in SEQ ID NOs: 18 and 19, respectively, again with the former sequence being 5' to the latter. In addition to these partial sequences, the complete coding sequences of U4, U9, and U10 have now been determined, and are shown as SEQ ID NOs: 13, 14, and 15, respectively. [U9 (represented in part by SEQ ID NO: 11 and in full by SEQ ID NO: 14) is now known to have the same cDNA sequence as that published by Saheki et al., Biochem. Biophys. Res. Comm. 185:240–245, 1992 for the cDNA encoding preproelafin. The amino acid sequence of elafin, an elastase-specific inhibitor found in human skin, was previously published by Wiedow et al., J. Biol. Chem. 265:14791–14795, 1990.] The novel genes of the invention are specifically described in detail below.

It is not expected that every candidate tumor suppressor gene will be expressed at a lower-than-normal level in a given tumor cell, or that an assay based upon any one candidate tumor suppressor gene will be useful as a universal cancer detection tool. Rather, it is believed that decreased expression of a given gene will prove to be a marker for certain types of cancers, while other genes will be markers for other types of cancers, so that a battery of tests utilizing a number of probes of the invention will be desirable. There may also be varying levels of expression of a given candidate tumor suppressor gene even between cells of a given type of cancer, further emphasizing the need for reliance on a battery of tests rather than a single test. It is well established in the cancer literature that tumor cells of the same type (e.g., breast tumor cells) may not express uniformly increased expression of individual oncogenes or uniformly decreased expression of individual tumor suppressor genes. Therefore, altered expression of any given candidate tumor suppressor gene is not expected to be seen in every patient sample examined, even among samples from similar types of tumors. With respect to oncogenes, altered expression in 10–50% of those tumors examined is typically found.

In other preferred embodiments, the amount of hybridization of the nucleic acid with RNA from precancerous or cancerous cells in the human is less than one third the level detected with a normal cell, more preferably less than one tenth the level, or even more preferably is undetectable.

In a second aspect, the invention features a method for identifying a drug useful for treatment of a cancer cell. The method includes the steps of identifying a candidate class II tumor suppressor gene, expression of which is suppressed [i.e., significantly diminished (e.g., by two thirds or more)] in a given type of cancerous cell from a given type of tissue, compared to a normal cell in the same type of tissue;

providing a first and a second sample of that given type of cancerous cell;

treating the second sample with a candidate drug; and determining the level of expression of the gene in the second sample after treatment with the candidate drug, wherein a drug which increases the level of expression of the gene in the second sample, compared to the level of expression of the gene in the untreated first sample, is potentially useful for treatment of the given type of cancer cell, and perhaps for other types of cancer cells, as well.

Generally, the candidate class II tumor suppressor gene and the level of expression of that gene are identified or determined as discussed herein. Potentially useful drugs may be chosen from, for example, those which alter signal transduction pathways, or which facilitate or induce demethylation of methylated residues on DNA. Such drugs may increase tumor suppressor gene expression by, for example, (1) increasing tumor suppressor gene messenger RNA synthesis, mRNA processing, or protein synthesis; (2) decreasing RNA degradation or protein degradation; or (3) affecting a post-translational mechanism such as phosphorylation.

In a related aspect, the invention features methods for treating a patient who has cancer. One such method involves the steps of identifying, in a human, a cell having a low level of expression of a candidate tumor suppressor gene compared to a normal cell, and treating that cell with a drug identified as one which raises the level of expression of that candidate tumor suppressor gene in cancer cells. Stated another way, the method of treatment includes the steps of identifying a patient with a cancer cell characterized by a low level of expression of a candidate tumor suppressor gene, compared to the level of expression of such gene in a normal cell of the same tissue type as the cancer cell; and either treating the cancer cell with a compound which raises the level of expression of the gene in the cancer cell, or introducing into the cancer cell a nucleic acid encoding the gene. Preferably, the nucleic acid would include an expression control element permitting expression of the gene in the cancer cell. Treating patients with such drugs or gene therapy provides a means to control or eliminate their cancers.

The invention also includes an isolated DNA which hybridizes under high-stringency conditions to any one of the sequences shown as SEQ ID NOs: 3–19 (preferably one of SEQ ID NOs: 1–10, 12–13, or 15–19), including but not limited to an isolated DNA which contains a sequence identical to any one of such sequences. The term "isolated DNA" denotes a DNA that is free of the genes which, in the naturally-occurring genome of the organism from which the DNA of the invention is derived, flank the candidate tumor suppressor gene that hybridizes to the sequence shown in the applicable SEQ ID NO. The term therefore includes, for example, a cDNA encoding the applicable candidate tumor suppressor gene product; a recombinant DNA which is incorporated into a vector, into an autonomously replicating plasmid or virus, or into the genomic DNA of a prokaryote or eukaryote; or a genomic DNA fragment produced by PCR or restriction endonuclease treatment. It also includes a recombinant DNA which is part of a hybrid gene encoding additional polypeptide sequence.

Other features and advantages of the invention will be apparent from the following description of the preferred embodiments thereof, and from the claims.

DETAILED DESCRIPTION

The drawing is first briefly described.

Drawing

FIGS. 1A and 1B illustrates the DNA sequence of a cDNA encoding human connexin 26 (C×26), and the amino acid sequence deduced therefrom.

Candidate Tumor Suppressor Genes

Candidate class I and class II tumor suppressor genes are generally described above. These candidate tumor suppressor genes can be identified as described by Sager, supra, or as described by Trask et al., 87 *Proc. Natl. Acad. Sci. USA* 2319, 1990; Yaswen et al., 87 *Proc. Natl. Acad. Sci. USA* 7360, 1990; Lee et al., 88 *Proc. Natl. Acad. Sci. USA* 2825, 1991; or Lee et al., 89 *Proc. Natl. Acad. Sci. USA* 2504, 1992, wherein specific subtractive hybridization methods are provided. All of these publications are herein incorporated by reference. In addition, the subtractive hybridization method described below may be used. The subtractive hybridization method is particularly advantageous in screening for candidate tumor suppressor genes since it provides a positive selection procedure.

The following is a specific example of such a subtractive hybridization procedure used to screen for candidate tumor suppressor genes involved in breast cancer. This example is not limiting in the invention and those of ordinary skill in the art will recognize that many variations to this method can be used with equivalent efficacy in identifying useful candidate tumor suppressor genes.

Identification and Isolation of Candidate Genes

In this example the medium, DFCI-1, described by Band and Sager, 86 *Proc. Natl. Acad. Sci., USA* 1249, 1989 was used because of its unique ability to support similar growth rates of both normal and tumor-derived human mammary epithelial cells. No other medium described in the literature is known to have this capacity. cDNA rather than genomic DNA was used for screening since the cDNAs are smaller and easier to manipulate than their genomic counterparts, and are present in multiple copies. Recovery of such cDNAs allows their use as probes to isolate the equivalent genomic DNA. Further, the cDNA can be expressed in a expression vector to produce the tumor suppressor gene product, and thus allow production of antibodies to that product for use in the methods described herein. The cDNA may be genetically manipulated so that it encodes only a chosen portion of the full-length gene product, resulting in expression of a defined oligopeptide fragment of the tumor suppressor gene product that may be used to generate antibodies useful for detecting the full-length gene product. Alternatively, the oligopeptides may be chemically synthesized. Design and production of such defined fragments may be accomplished by standard methods.

The normal cells used in the methods described herein were derived from a strain 76N established from discarded reduction mammoplasty tissue as described by Band and Sager, supra. These cells are diploid and senesce after 15–20 passages. The tumor cells were derived from an aneuploid cell line established from a pleural effusion as described by Band et al., 1 *Genes, Chromosomes, and Cancer* 48, 1989 and Band et al., 50 *Cancer Research* 7351, 1990. However, any cells used for subtractive hybridization can be derived from any individuals, and substituted as described below.

Primary tumor cells or metastatic cells can be used. In this example, both parental cell populations were grown in DFCI-1 medium at similar population doubling times of about 30 hours. These cells were harvested at 70% confluency directly into 4M guanidinium isothiocyanate, 0.5M sodium citrate, and 0.1M β-mercaptoethanol for RNA preparation. Total RNA was extracted from the cells by lysis in the guanidium isothiocyanate mixture, and poly(A)+RNA purified by two cycles of affinity chromatography on oligo(dT) cellulose by standard technique. The cDNA was synthesized using Moloney murine leukemia virus reverse transcriptase from Bethesda Research Laboratories with an oligodeoxynucleotide oligo(dT)$_{12-18}$ as a primer.

The candidate tumor suppressor genes described in Sager, 1989 supra, Lee et al., 1991 supra, and Lee et al., 1992 supra were isolated by the following method. The $^{32}$P pre-labeled SS cDNA from 76N cells was hybridized with a 10-fold excess of tumor poly(A)$^+$ mRNA from 21MT-2 cells (Band et al., Cancer Research 1990). 500 ng fibronectin (FN) mRNA, prepared by in vitro transcription was added to subtract out FN cDNA, which is present at high abundance in the mRNA of the normal cells. The hybridization reaction mixture was loaded onto a hydroxylapatite column maintained at 60° C. and eluted with 0.1M phosphate buffer (pH 6.8). After rerunning the effluent through the column three times, the effluent was collected and rehybridized as above (2nd subtraction) without added FNm RNA. The final effluent was concentrated to 100 µl, a sample was removed for quantitation, and the rest frozen for subsequent screening.

cDNA from 76N poly(A)$^+$ RNA was used to produce a recombinant library in the phagemid lambda Zap II (Stratagene Corp., La Jolla, Calif.) by procedures recommended by the vender. The 76N library was screened by differential hybridization using the $^{32}$P random-primer labelled subtracted cDNA probe against the tumor specific cDNA. After a secondary screening the differentially expressed clones were isolated, and the inserts were amplified by PCR from phage using T3 and T7 sequences as primers. After gel electrophoresis, the PCR products were purified by phenol/chloroform extraction from agarose and $^{32}$P random-primer labelled for RNA northern analysis.

Total RNA (20 ug) was heat denatured at 68° C. for 15–20 min. followed by electrophoresis in 1.2% agarose-formaldehyde gels and transferred to nylon membranes (Zeta-probe, BioRad); prehybridization and hybridization were performed as described by Haskill et al., 87 *Proc. Natl. Acad. Sci, USA* 7732, 1990. Sequencing of cloned DNA was performed either directly or on exonuclease III-deleted derivatives. These deletion derivatives were generated using a Promega Erase-a-Base kit but can be generated by using other standard technique. Sequencing was carried out by a dideoxy chain termination method with T7 DNA polymerase (Pharmacia). Parallel reactions were also performed with dGTP analogs (Pharmacia) when necessary to resolve sequence compressions.

In one subtraction, 50 clones were recovered. After two rounds of screening, seven different clones showed unique or highly preferential expression in normal cells compared to tumor cells. The clones were identified by northern hybridization using standard techniques. The size range of mRNAs varied from 0.6 kb to almost 5 kb. These clones include genes expressed at rare to high abundance in mRNAs.

One clone, termed clone 1–3, is expressed in four normal strains but not in a series of tumor-derived lines. It has been shown by sequence comparison in GENBANK to encode the human homolog of rat connexin 26 (Cx26), a gap junction protein the DNA sequence of which is provided by Zhang and Nicholson 109 *Journal Cell Biology* 3391, 1989. The DNA and deduced amino acid sequence of human connexin 26 (SEQ ID NO: 2) is given below in FIGS. 1A and 1B. This cDNA clone has a single long open reading frame that extends to a stop codon at base 881, and encodes a putative protein of 226 amino acid residues with a predicted molecular mass of ~26,000 daltons.

Preceding the initiator ATC, 23 nucleotides upstream from ATG, is a consensus splice accepter signal (TTTCCAG), raising the possibility that splicing occurs at this site to create two sizes of human Cx26 transcripts. This signal sequence is not present in the 5' region of the rat Cx26 sequence, which does not produce two transcripts. The 3' untranslated regions contains a possible polyadenylation signal sequence AATAAA positioned 87 nucleotides upstream from the poly(A)$^+$ tail. At nucleotide positions 1326, 1623, 1664 and 2082 a putative instability sequence ATTTA, is present, which may be involved in posttranscriptional regulation. The overall nucleotide homology between human and rat Cx26 is 86.2% within the open reading frame. The amino acid sequence deduced from the human cDNA is 92.5% identical to rat Cx26. However, the 5' and 3' untranslated regions show no significant similarity between human and rat.

To confirm the intracellular location of gap junction proteins in human mammary epithelial cells, we examined cells by immunofluorescence using anti-Cx26 or anti-Cx43 antibodies. Specific fluorescent spots were found at membrane contact sites of 76N cells (a normal human mammary epithelial cell line), whereas no fluorescence staining was observed with 21MT2 cells (a human breast tumor cell line). When fixed cells were treated with preimmune serum, the immunoreactivity failed to show discrete punctate staining at the cell membrane. Failure to localize Cx26 or Cx43 protein at the junctional areas of 21MT2 cells is consistent with the lack of connexin mRNA expression observed in breast tumor cells.

To assess the relative periodicity of connexin gene expression during the cell cycle, normal mammary epithelial cells were synchronized in G$_1$ by lovastatin (15 µM/24 hours), released from lovastatin-induced arrest by the addition of 2 mM mevalonate, and then sampled at 3 hour intervals over the next 33 hours. Cx26 and Cx43 transcript levels were analyzed by Northern blot analysis of total RNA prepared from samples taken at indicated times. The progress of the cells through the cell cycle was monitored by [$^3$H]thymidine incorporation and by the level of histone H4 mRNA in Northern blot analysis. Histone H4 was induced in S phase at 18 hour. The time of appearance of histone H4 message coincided with the peak period of DNA synthesis as measured by [$^3$H]-thymidine incorporation. The upper Cx26 transcript increased at 6 hr. to a moderate steady state level until 21 hr, near the end of S phase, when both Cx26 transcripts showed a further increase in G$_2$. In contrast to Cx26 mRNA, Cx43 expression during the cell cycle was relatively invariant. Considering the assumed similarity of their functions, the expression of both connexins during the cell cycle might be expected to show a similar regulation pattern. Thus, the difference in cell cycle regulation of Cx26 and Cx43 is quite surprising.

Connexins are structural proteins that surround the channels of which gap junctions are composed; the channels in turn provide direct communication between adjacent cells. Gap junctions have been postulated to play a growth regulatory role, on the basis of numerous correlations between growth control and junctional communication. Of these, one of the earliest and still the most striking is Stoker's experiment in which polyoma-transformed BHK cells were inhibited from colony formation by contact (later shown to be junctional communication) with a monolayer of normal BHK cells. Recent experiments by Loewenstein and coworkers and others have correlated post-translational modulation of junctional communication with growth inhibition. Our results, in contrast, suggest transcriptional regulation. This opens the possibility for experimental and clinical modulation at the level of transcription as described below.

A clone termed clone 2-3 encodes glutathione-S-transferase pi, identified by sequence comparison with known genes in GENBANK. The DNA sequence for glutathione-S-transferase pi is provided by Moscow et al., 49 *Cancer Research* 1422, 1989. This protein is a well-characterized enzyme, present in many cell types, that has detoxifying activity against many lipophilic toxic agents including carcinogens. We have found that it is down-regulated in a number of mammary tumor-derived cell lines, both primary and metastatic, but strongly expressed in normal and immortalized mammary epithelial cells grown in culture. However, this gene is expressed in some breast tumors, and this distinction between tumors that do and those that do not express the gene may itself have prognostic value.

A clone originally termed clone 19, and now referred to as CaN19 (Lee et al., 1992 supra), represents a gene expressed in normal mammary epithelial cell strains but not in tumor-derived cell lines. The DNA sequence (and corresponding amino acid sequence, or "gene product") of CaN19 is shown as SEQ ID NO: 1 below. Sequence comparisons have shown that CaN19 is a member of the S100 gene family, encoding small Ca$^{++}$ binding proteins (about 10 kD) with diverse functions. These proteins have two "EF hands", domains where Ca$^{2+}$ is bound, in contrast to calmodulin proteins which have four. The S100 beta protein is a major constituent of glial cells, whereas related proteins are expressed in differentiated but not in undifferentiated PC 12 (rat pheochromocytoma) cells. CaN19 is also related in structure to the small regulatory subunit of calpactin, p11. MRP8 and MRP14 are also related and are S100 proteins expressed by macrophages during chronic inflammation. Calabretta et al., 261 *J. Biol. Chem.* 12628, 1986. Another related protein, calcyclin, has been found in serum-induced cycling cells, but not in quiescent cells, and in leukocytes from CML patients. A related mouse protein is also cell cycle induced. The possibility that calcyclin expression might be cancer related is particularly interesting in view of our evidence that CaN19 is not expressed in breast tumor cells. CaN19 appears to be negatively regulated in tumors, in contrast to calcyclin. Other related proteins are described by Kligman and Hilt 13 TIBS 437, 1988.

Other genes which are useful in the present invention include NB-1 described by Yaswen et al., supra; keratin 5 as described by Trask et al., supra, the DNA sequence of which is published in 8 *Molecular Cell Biology* 486, 1988; and small proline-rich protein (spr-1), the sequence of which is published in 18 *Nucl. Acid Res.* 4401–4407, 1990. The latter gene is known to be expressed at higher levels following treatment with ultraviolet radiation, suggesting that the protein may have a DNA repair function. Thus, spr-1 is a very promising gene for further investigation. The as-yet unidentified novel gene U10 (SEQ ID NO: 12) was also identified by the method of subtractive hybridization described above.

In further experiments, an adaptation of the subtractive hybridization technique was used which proved to be less laborious and more efficient for cloning of candidate tumor suppressor genes, including rarely expressed genes, than the hydroxyapatite column method. This method utilizes a biotinylation-based subtraction procedure (Schweinfest et al., 7 *Genet. Annal. Techn. Appl.* 64–70, 1990; Swaroop et al., 19 *Nucl. Acids Res.* 1954, 1991), instead of hydroxyapatite as previously used. In this procedure, a single strand phagemid cDNA library from normal cell polyA$^+$ mRNA is hybridized with excess biotinylated tumor polyA$^+$ mRNA, and the resulting double stranded sequences are removed by binding to streptavidin. The remaining single-stranded phagemid cDNAs are converted to double-stranded form and used to transform bacterial host cells. The resulting subtracted cDNA library is differentially screened with total cDNA from normal and tumor cells. This method produced some 20 additional cloned cDNAs, including some which, upon partial sequencing, proved to have been previously identified by others, and some which appear to be novel. The previously-identified genes which were found by this method to be candidate tumor suppressor genes potentially useful in the methods of the invention include genes encoding human amphiregulin (the full sequence of which can be found in GENBANK at locus HUMARXC, Accession #M30704); thymosin beta-4 (locus HUMTHYB4, Accession #M17733); gamma actin (locus HUMACTCGR, Accession ##X04098, K00791, M24241); calpactin light chain (p11) (locus HUMCALPA1L, Accession #M81457); HBp17 (locus HUMHEPBP, Accession #M60047), myosin regulatory light chain (locus HUMMRLCM, Accession #X54304); v-fos transformation effector protein (locus HUMFTE1A, Accession #M84711); and the mitochondrial genome-encoded proteins NADP-dehydrogenase (locus HUMMTHSXX, Accession #V00662); Co III (locus HUMMTHSXX, Accession #V00662); and ATPase6 (locus HUMMTCG, Accession ##J01415, M12548, M58503, M63932, and M639333). Also found by this method was the gene encoding preproelafin, referred to herein as U9 [SEQ ID NOs: 11 (partial sequence) and 14 (full sequence)], and several additional genes which, on the basis of the DNA sequences set forth as SEQ ID NOs: 3–10, 12–13, and 15–19, respectively, appear to be novel sequences not previously entered into GENBANK. The portion of the cDNAs so sequenced represents at least part of the coding region and/or part of the 3' untranslated region of each cDNA; some of the sequences shown (SEQ ID NOs: 13, 14 and 15) are complete cDNA sequences. Still other genes can be identified as described above using northern analysis of isolated clones and determining whether tumor cell expression of the gene is reduced by at least ⅔ compared to normal cells.

Most or all of the genes described herein have been found to be expressed at a low but detectible level in at least some tumor cell lines (which is taken to be an indication that the coding sequence is intact in these cells), and thus appear to be candidate class II rather than class I tumor suppressor genes in these tumors. Another indication that a particular candidate tumor suppressor gene falls within class II in a particular tumor is a normal-appearing Southern blot of the tumor's genomic DNA when probed with the tumor suppressor gene cDNA. (Some point mutations, small deletions or rearrangements might not be detected, of course.) Candidate class I tumor suppressor genes, in which the coding sequence of the gene is altered in a way to yield no biologically active gene product or an altered gene product, could also be detected by the differential hybridization screening method of the invention if the genetic alterations are such that (1) no detectable mRNA is transcribed from the mutant gene, or (2) the mRNA transcribed from the gene is sufficiently different from wild type that it cannot hybridize to the hybridization probe utilized, or (3) the mRNA has an altered sequence resulting in a different location on a Northern gel than the normal mRNA, or (4) the mRNA is hydrolyzed by the cell rapidly after transcription. The alternative method of detection disclosed herein, in which an antibody to the wild type candidate tumor suppressor gene product is used to detect gene expression in cell samples, would also be useful for identifying candidate Class I tumor suppressor genes, and for detecting their expression in a given cell sample, if the mutations in the coding sequence of the gene are such that (1) no stable gene product is expressed by the mutant gene, or (2) the gene product that is expressed is so altered that the antibody utilized cannot bind to it.

Diagnostic applications

Class II genes are of particular interest because the suppressor gene has not been lost, and may therefore be available for up-regulation by drugs or other treatment. Restoration of suppressor gene function by regulatory intervention offers new opportunities in the design of novel drugs for cancer therapy.

Both Class I and Class II genes are immediately valuable for early diagnosis and prognosis, which are especially pressing needs in breast cancer where the course of the disease is so unpredictable. Some genes expressed preferentially in normal cells may not have tumor suppressor functions. They are nonetheless useful as diagnostic markers.

The candidate suppressor genes described herein represent just the "tip of the iceberg" with respect to loss-of-function genes that may be useful in diagnosis, prognosis, and therapy. Genes with numerous and diverse functions are anticipated to participate in protecting the long-lived human species from cancer. They include DNA repair genes that maintain genomic integrity and stability, genes that promote irreversible steps in differentiation, and genes that regulate proliferation. Cancer starts at the cellular level, but becomes a systemic disease, and at that point, systemic mechanisms of protection play important roles. These include cell—cell communication by gap junctions, paracrine regulation by growth factors and cytokines, protection by the immune system, control of angiogenesis, and the regulation of tumor invasion. For each of these, specific genes encode key proteins whose loss may facilitate neoplasia. The experimental system described herein allows early recognition of aberrant tumor suppressor and diagnostic genes.

As discussed above, both candidate class I and candidate class II tumor suppressor genes can be used for diagnosis of cancer. All of those genes described above, and other genes identified in a similar manner, are potentially useful for diagnosis of cancerous conditions. For example, they are particularly useful for identification of cancerous cells in solid tumors, such as in breast cancer. Once a lump is detected in a mammogram, or by other means in a breast, a portion of that lump may be removed and analyzed by northern analysis or by in situ hybridization using the cloned gene (or antibodies to the gene product produced by standard techniques) to determine whether the level of expression of the candidate tumor suppressor gene is normal or at a reduced level. If it is at a reduced level, this will be indicative that the cells in that lump are cancerous or pre-cancerous and appropriate steps may be taken to either remove or treat those cells in vivo.

Similarly, routine diagnosis can be obtained in a manner similar to a papsmear in which cells are taken from a human and tested by hybridization with any one or more of the above candidate tumor suppressor genes or by immune complex formation with antibodies to the gene products. Such testing will allow earlier diagnosis of cancerous conditions than has previously been possible.

Those of ordinary skill in this art will recognize that the northern analysis and in situ hybridization or immune complex formation can be carried out by any of a number of standard techniques. For example, the DNA of a candidate tumor suppressor gene or its equivalent cDNA may be used as a probe for RNA transcribed from those genes in cells to be tested. Similarly, DNA which hybridizes to the RNA produced by such genes can also be used.

The cDNA or its equivalent may be placed in expression vectors to cause production of candidate tumor suppressor gene products which may be purified and used to isolate polyclonal or monoclonal antibodies to those candidate tumor suppressor gene products. Those particular antibodies which are specific for (i.e., form readily detectible immune complexes with) the candidate tumor suppressor gene product can be identified by standard procedures. Generally, it is preferred that a specific monoclonal antibody be identified so that a large amount of that antibody can be readily produced and used in diagnostic procedures. Immunoprecipitation by antibodies of candidate tumor suppressor gene products is performed by standard methodology such as western blotting.

These diagnostic methods can be adapted for use as a way to monitor changes in the level of expression of a given candidate tumor suppressor gene in a given patient over time. This would be useful, for example, as a routine measure for monitoring for the presence of cancer in apparently healthy subjects, much as pap smears and mammograms are used. This technique relies upon the normal expression of a given candidate tumor suppressor gene product in a readily obtainable biological fluid such as blood, urine, or saliva. A baseline normal level of expression of the gene product would be established by analyzing samples taken from the subject over the years, or by comparison with standards obtained from other, disease-free individuals. A drop in the amount of the gene product present in a given sample would be an indication of the presence of tumor cells in the subject. Alternatively, the method could be adapted to serve as a means for following the clinical progression of a tumor, wherein increases or decreases in the level of the gene product in the analyzed sample would be indicative of decreasing or increasing tumor load, respectively.

The above-described method for assaying a biological fluid will work reliably only if the candidate tumor suppressor gene product is normally a secreted protein. Whether or not a given gene product is secreted can be determined empirically (e.g., by using an antibody specific for the gene product), or may be predicted by the presence of a secretion signal sequence in the cDNA (e.g., as taught by Von Heijne, 133 *Eur. J. Biochem.* 17–21, 1983) in accordance with standard methods.

Screening for and Treatment with Transcription- and/or Translation-increasing Drugs As generally discussed above, candidate class II tumor suppressor genes can be used to identify useful drugs for treatment of cancers. This may be accomplished by standard procedures by culturing cells which include tumor suppressor genes (which are either expressed at normal or subnormal levels) and treating those cells with a variety of drugs to determine which drugs increase the level of expression of the candidate tumor suppressor gene product within those cells. It is preferred that a cancerous cell be used in such a procedure since the increased level of expression of the candidate tumor suppressor gene product will be more readily detected in such a cell, and the drug may work only on genes the expression of which is lower than normal. Identification of the increase in tumor suppressor gene expression can be analyzed by standard northern or in situ analysis or by antibody testing. Alternatively, rather than looking for expression of the tumor suppressor gene, the concomitant increase in a function of that gene may be detected by standard techniques. Two examples illustrating such a procedure are given below. In these examples, phorbol myristate acetate (PMA) is found to increase expression of the Cx26 tumor suppressor gene in tumor cells but not in normal cells, while azadeoxycytidine increases the level of expression of the CaN19 candidate tumor suppressor gene in tumor cells but not in normal cells.

Once the appropriate drug is identified, it may be administered to humans who are identified as containing cells having a reduced level of the tumor suppressor gene product. This may be accomplished either by direct administration of the drug at the tumor site or by systemic treatment with the drug.

Drug-induced Stimulation of CaN19 mRNA Expression

In an analysis of the effects of certain drugs on induction of CaN19 expression, exponentially growing normal and tumor cells were treated with the following agents (5Br-cAMP, 1 mM; forskolin, 10 uM; PMA, 100 ng/ml; retinoic acid, 1 uM; A23187, 0.5 uM; actinomycin D, 5 ug/ml; cycloheximide, 10 ug/ml; okadaic acid, 5 ng/ml; TGF-β, 1 ng/ml; prolactin, 1 mg/ml; β-estradiol, 2 nM; 5-aza-2'-deoxycytidine, 1 uM–100 uM; all purchased from Sigma Chemical Co. except TGF-β from Collaborative Research Inc.) (Lee et al., 1992 supra). To study the effect of azadeoxycytidine, cells were plated at low density (~25% confluency) and incubated in the presence of various concentrations of drug. Cells were washed, retreated with drug in fresh medium for another 2 days, and then harvested for RNA analysis (~70% confluency). The steady state levels of mRNA were examined by Northern blot analysis with RNA extracted from normal and tumor cells at different time points (0, 1, 3, 6, 12, and 24 hours) after each drug treatment. Additions of 5Br-cAMP, forskolin, PMA, retinoic acid, actinomycin D, cycloheximide, A23187, or okadaic acid were without noticeable effect on the level of expression of CaN19 mRNA in tumor cells. In contrast, exposure of mammary tumor cells to azadeoxycytidine induced the expression of CaN19-specific RNA. The level of expression of CaN19 in normal cells was not affected by azadeoxycytidine treatment. These findings suggest that DNA methylation plays a direct role in control of CaN19 gene expression in tumor cells. Since aza-dCyd is a well-established DNA demethylating agent, it is very likely that treatment with this drug demethylated transcription binding sites in CaN19 and possibly in other unidentified genes as well. Although systemic treatment with aza-dCyd itself is said to be toxic and tumorigenic (Harrison et al., *Proc. Natl. Acad. Sci. USA* 80:6606–6610, 1983; Carr et al., *Carcinogenesis* 5:1583–1590, 1984), these results provide insight into a possible mechanism for switching on candidate tumor suppressor genes in tumor cells, and suggest testing other DNA demethylating agents for antitumor potential.

Drug-induced Stimulation of Cx26 mRNA Expression

Two different breast cancer cell lines, one from a primary tumor and one from a metastatic cell line, were found to have significantly reduced levels (compared to levels in normal breast cells) of connexin 26 expression by northern analysis, as discussed above. A short treatment of these cells with phorbol myristate acetate (PMA) induced the expression of mRNA in these cells, while treatment with certain other drugs that affect signal transduction pathways was found to have no effect on C×26 expression in these cells at the concentrations tested. Specifically, growing 21 PT cells (Band et al., *Cancer Research* 1990; derived from a primary tumor) were treated with 100 ng/ml PMA, 1 mM dBc-cAMP, 1 μM retinoic acid, 5 μg/ml actinomycin D, 10 μg/ml cycloheximide, 5 ng/ml okadaic acid, 2 nM β-estradiol, or 1 ng/ml TGFβ at time zero in a series of dishes. At time points from 0 to 48 hours after exposure to drug, samples were taken for RNA extraction and northern blot analysis. In the PMA-treated cells, expression of connexin 26 was observed by 3 hours, peaking at 6–12 hours (at 25% normal cell levels) and decreasing by 24 hours. Similar results were obtained with 21MT-2 cells, another tumor cell line. In contrast, PMA treatment of normal cells did not increase the level of C×26 gene expression above control levels.

In order to see whether C×26 mRNA stimulation in PMA-treated tumor cells leads to protein synthesis, immunofluorescence staining with anti-C×26 antibody and scrape-loading dye transfer experiments were performed at various times after PMA treatment, using several mammary tumor cell lines. C×26 proteins were not detected at cell to cell junctional areas nor was junctional communication detected between cells. Neither method was sensitive enough to detect a very weak signal, which might have resulted from the short half-life of the induced mRNA.

Gene Therapy

As generally discussed above, tumor suppressor genes of both class I and class II may be employed in gene therapy methods in order to increase the amount of the expression products of such genes in cancer cells. Although such gene therapy is particularly appropriate for use in cells, both cancerous and precancerous, in which the level of a particular tumor suppressor gene product is diminished compared to normal cells, it may also be useful to increase the level of expression of a given tumor suppressor gene even in those tumor cells in which the gene is expressed at a "normal" but perhaps not optimal level.

21MT-2 cells, a line of cultured breast tumor cells (developed in this laboratory) in which the level of C×26 mRNA is undetectable, were transfected with a plasmid construct containing the full-length cDNA corresponding to C×26 linked to appropriate expression control elements. Unlike the untransfected cells, the transfectants expressed significant amounts of C×26 protein. Furthermore, the transfected cells were found to assemble the C×26 protein into gap junctions that functioned in cell—cell communication in the same manner as described for normal mammary epithelial cells. These results indicate that, by transferring a candidate tumor suppressor gene along with expression control elements into a tumor cell which does not express the gene from its own genome, tumor cells can be induced to produce functional candidate tumor suppressor gene product at high levels.

Gene therapy would be carried out according to generally accepted methods: for example, as described by Friedmann in *Therapy for Genetic Disease*, T. Friedman (ed.), Oxford Univ. Press, 1991, pp.105–121. Cells from a patient's tumor would first be analyzed by the diagnostic methods described above, in order to ascertain which if any of the candidate tumor suppressor genes are expressed at a significantly lower than normal level (or not at all) in the tumor cells. A virus or plasmid containing a copy of such a tumor suppressor gene linked to expression control elements and capable of replicating inside the tumor cells would then be injected into the patient, either locally at the site of the tumor or systemically (in order to reach any tumor cells that may have metastasized to other sites). If the transfected gene is not permanently incorporated into the genome of each of the targeted tumor cells, the treatment may have to be repeated periodically.

Other embodiments are within the following claims.

What is claimed is:

1. A method of determining, by in situ hybridization, whether a sample containing a test cell from human breast tissue is (a) normal, or (b) cancerous, said method comprising the steps of:

contacting the mRNA of said test cell in situ with a nucleic acid probe comprising a nucleotide sequence at least 15 nucleotides in length which is complementary to a portion of the coding sequence or a candidate tumor suppressor gene, said gene being one which is normally expressed in normal cells of human breast tissue; and determining whether said probe hybridizes to said mRNA under high stringency conditions selected to permit hybridization of said probe to normal cells of human breast tissue, wherein the failure to hybridize to said mRNA is an indication that said test cell is cancerous; provided that said gene encodes connexin 26, connexin 43, preproelafin, CaN19 is protein, or HBp17.

2. The method of claim 1, said method comprising the additional steps of:

contacting the mRNA of said test cell in situ with a second nucleic acid probe comprising a nucleotide sequence at least 15 nucleotides in length which is complementary to a portion of the coding sequence of a second candidate tumor suppressor gene different from said first candidate tumor suppressor gene, said second gene being one which is normally expressed in normal cells of human breast tissue; and determining whether either of said first and second probes hybridizes to said mRNA under high stringency conditions selected to permit hybridization to normal cells of human breast tissue, wherein failure of either said first probe or said second probe to hybridize with said mRNA is an indication that said test cell is cancerous; provided that said second gene encodes connexin 26, connexin 43, preproelafin, CaN19 protein, or HBp17.

3. The method of claim 1, said method comprising the additional steps of:

contacting the mRNA of said test cell in situ with a second nucleic acid probe comprising a nucleotide sequence at least 15 nucleotides in length which is complementary to a portion of the coding sequence of a second candidate tumor suppressor gene different from said first candidate tumor suppressor gene, said second gene being one which is normally expressed in normal cells of human breast tissue; and determining whether either of said first and second probes hybridizes to said mRNA under high stringency conditions selected to permit hybridization of both of said probes to normal cells of human breast tissue, wherein failure of either said first probe or said second probe to hybridize with said mRNA is an indication that said test cell is cancerous; provided that said second gene includes a sequence which hybridizes under stringent conditions to SEQ ID NO: 3 (U1), SEQ ID NO: 4 (U2), SEQ ID NO: 8 (U6), SEQ ID NO: 9 (U7), SEQ ID NO: 10 (U8), SEQ ID NO: 11 (U9), SEQ ID NO: 14 (U9), SEQ ID NO: SEQ ID NO: 16 (U1), SEQ ID NO: 17 (U1), SEQ ID NO: 18 (U2), or SEQ ID NO: 19 (U2).

4. A method of confirming, by in situ hybridization, a diagnosis that a given fraction of cells in a human breast tissue sample are cancerous, said method comprising the steps of:

contacting the mRNA of said sample in situ with a nucleic acid probe comprising a nucleotide sequence at least nucleotides in length which is complementary to a portion of the coding sequence of a candidate tumor suppressor gene, said gene being one which is expressed in normal cells of human breast tissue at a given control level; and determining whether the fraction of cells in said sample which, under high stringency hybridization conditions selected to permit hybridization to normal cells of human breast tissue, fail to exhibit detectable hybridization to said probe is approximately equivalent to said given fraction of cells previously diagnosed as being cancerous, said equivalence of fractions being a confirmation of said diagnosis; provided that said gene encodes connexin 26, connexin 43, preproelafin, CaN19 protein, or HBp17.

5. A method for determining the presence of cancerous cells in the breast tissue of a patient, which method comprises the steps of:

providing a nucleic acid probe comprising a nucleotide sequence at least 15 nucleotides in length which is complementary to a portion of the coding sequence of a candidate tumor suppressor gene, said gene encoding connexin 26, connexin 43, preproelafin, CaN19 protein, or HBp17;

obtaining from a patient a first sample of breast tissue, said first sample potentially comprising cancerous cells;

providing a second sample of breast tissue, substantially all of the cells of said second sample being non-cancerous;

contacting in situ said nucleic acid probe under stringent hybridizing conditions with RNA of each of said first and second tissue samples, said hybridization conditions being selected to permit hybridization of said probe to non-cancerous cells of breast tissue; and comparing (a) the in situ hybridization of said nucleic acid probe with said first tissue sample, with (b) the in situ hybridization of said nucleic acid probe with said second tissue sample, wherein hybridization with said second tissue sample but not with said first tissue sample indicates the presence of cancerous cells in said first tissue sample.

6. A method of determining, by in situ hybridization, whether a sample containing a test cell from human breast tissue is (a) normal, or (b) cancerous, said method comprising the steps of:

contacting the mRNA of said test cell in situ with a nucleic acid probe comprising a nucleotide sequence at least 15 nucleotides in length which is complementary to a portion of the coding sequence of a candidate tumor suppressor gene, said gene being one which is normally expressed in normal cells of human breast tissue; and determining whether said probe hybridizes to said mRNA under high stringency conditions selected to permit hybridization to normal cells of human breast tissue, wherein the failure to hybridize to said mRNA is an indication that said test cell is cancerous;

provided that said gene includes a sequence which hybridizes under stringent conditions to SEQ ID NO: 3 (U1), SEQ ID NO: 4 (U2), SEQ ID NO: 8 (U6), SEQ ID NO: 9 (U7), SEQ ID NO: 10 (U8), SEQ ID NO: 11 (U9), SEQ ID NO: 14 (U9), SEQ ID NO: 16 (U1), SEQ ID NO: 17 (U1), SEQ ID NO: 18 (U2), or SEQ ID NO: 19 (U2).

7. The method of claim 6, said method comprising the additional steps of:

contacting the mRNA of said test cell in situ with a second nucleic acid probe comprising a nucleotide sequence at least 15 nucleotides in length which is complementary to a portion of the coding sequence of a second candidate tumor suppressor gone different from said first candidate tumor suppressor gene, said second gene being one which is normally expressed in normal cells of human breast tissue; and determining whether either of said first and second probes hybridizes to said mRNA under high stringency conditions selected to permit hybridization of both of said probes to normal cells of human breast tissue, wherein failure of either said first probe or said second probe to hybridize with said mRNA is an indication that said test cell is cancerous; provided that said second gene includes a sequence which hybridizes under stringent conditions to SEQ ID NO: 3 (U1), SEQ ID NO: 4 (U2), SEQ ID NO: 8 (U6), SEQ ID NO: 9 (U7), SEQ ID NO: 10 (U8), SEQ ID NO: 11 (U9), SEQ ID NO: 14 (U9), SEQ ID NO: 16 (U1), SEQ ID NO: 17 (U1), SEQ ID NO: 18 (U2), or SEQ ID NO: 19 (U2).

8. The method of claim 6, said method comprising the additional steps of:

contacting the mRNA of said test cell in situ with a second nucleic acid probe comprising a nucleotide sequence at least 15 nucleotides in length which is complementary to a portion of the coding sequence of a second candidate tumor suppressor gene different from said first candidate tumor suppressor gene, said second gene being one which is normally expressed in normal cells of human breast tissue; and determining whether either of said first and second probes hybridizes to said ERNA under high stringency conditions selected to permit hybridization of both of said probes to normal cells of human breast tissue, wherein failure of either said first probe or said second probe to hybridize with said mRNA is an indication that said test cell is cancerous; provided that said second gene encodes connexin 26, connexin 43, preproelafin, CaN19 protein, or HBp17.

9. A method of confirming, by in situ hybridization, a diagnosis that a given fraction of cells in a human breast tissue sample are cancerous, said method comprising the steps of:

contacting the mRNA of said sample in situ with a nucleic acid probe comprising a nucleotide sequence at least 15 nucleotides in length which is complementary to a portion of the coding sequence of a candidate tumor suppressor gene, said gene being one which is expressed in normal cells of human breast tissue at a given control level; and determining whether the fraction of cells in said sample which, under high stringency hybridization conditions selected to permit hybridization to normal cells of human breast tissue, fail to exhibit detectable hybridization to said probe is approximately equivalent to said given fraction of cells previously diagnosed as being cancerous, said equivalence of fractions being a confirmation of said diagnosis; provided that said gene comprises a sequence which hybridizes under stringent conditions to SEQ ID NO: 3 (U1), SEQ ID NO: 4 (U2), SEQ ID Nor 8 (U6), SEQ ID NO: 9 (U7), SEQ ID NO: 10 (U8), SEQ ID NO: 11 (U9), SEQ ID NO: 14 (U9), SEQ ID NO: 16 (U1), SEQ ID NO: 17 (U1), SEQ ID NO: 18 (U2), or SEQ ID NO: 19 (U2).

10. A method for determining the presence of cancerous cells in the breast tissue of a patient, which method comprises the steps of:

providing a nucleic acid probe comprising a nucleotide sequence at least 15 nucleotides in length which is complementary to a portion of the coding sequence of a candidate tumor suppressor gene, said gene comprising a sequence which hybridizes under stringent conditions to SEQ ID NO: 3 (U1), SEQ ID NO: 4 (U2), SEQ ID NO: 8 (U6), SEQ ID NO: 9 (U7), SEQ ID NO: 10 (U8), SEQ ID NO: 11 (U9), SEQ ID NO: 14 (U9), SEQ ID NO: 16 (U1), SEQ ID NO: 17 (U1), SEQ ID NO: 18 (U2), or SEQ ID NO: 19 (U2);

obtaining from a patient a first sample of breast tissue, said first sample potentially comprising cancerous cells;

providing a second sample of breast tissue, substantially all of the cells of said second sample being non-cancerous;

contacting in situ said nucleic acid probe under stringent hybridizing conditions with RNA of each of said first and second tissue samples, said hybridization conditions being selected to permit hybridization of said probe to non-cancerous cells of breast tissue; and comparing (a) the in situ hybridization of said nucleic acid probe with said first tissue sample, with (b) the in situ hybridization of said nucleic acid probe with said second tissue sample, wherein hybridization with said second tissue sample but not with said first tissue sample indicates the presence of cancerous cells in said first tissue sample.

* * * * *